United States Patent
Le Vot et al.

(10) Patent No.: US 9,662,602 B2
(45) Date of Patent: May 30, 2017

(54) METHOD OF SORTING PARTICLES OR PARTICLE CLUSTERS IN A FLUID FLOWING IN A CHANNEL

(75) Inventors: Sophie Le Vot, Le Pont de Claix (FR); Jean Berthier, Meylan (FR); Florence Rivera, Meylan (FR)

(73) Assignee: Commissariat a L'Energie Atomique, Paris (FR)

(*) Notice: Subject to any disclaimer, the term of this patent is extended or adjusted under 35 U.S.C. 154(b) by 901 days.

(21) Appl. No.: 12/437,992

(22) Filed: May 8, 2009

(65) Prior Publication Data
US 2009/0283456 A1   Nov. 19, 2009

(30) Foreign Application Priority Data
May 13, 2008   (FR) ...................................... 08 02577

(51) Int. Cl.
*B07C 5/12* (2006.01)
*B01D 43/00* (2006.01)
*B01L 3/00* (2006.01)
*G01N 15/02* (2006.01)

(52) U.S. Cl.
CPC ........ *B01D 43/00* (2013.01); *B01L 3/502761* (2013.01); *B01L 2200/0647* (2013.01); *B01L 2200/0652* (2013.01); *B01L 2200/0668* (2013.01); *B01L 2300/0816* (2013.01); *B01L 2400/0463* (2013.01); *G01N 2015/0288* (2013.01)

(58) Field of Classification Search
CPC ............................ B01D 43/00; G06F 11/2294
USPC ...................................... 209/18, 20, 136, 157
See application file for complete search history.

(56) References Cited

U.S. PATENT DOCUMENTS 5,587,128 A * 12/1996 Wilding et al. ................. 422/50
5,635,358 A *  6/1997 Wilding et al. ................ 435/7.2
5,858,187 A *  1/1999 Ramsey et al. ............... 204/452
(Continued)

FOREIGN PATENT DOCUMENTS

WO       WO 03/006133 A      1/2003

OTHER PUBLICATIONS

Search Report from French Priority Application No. 08 02577, Filed May 13, 2008.
(Continued)

*Primary Examiner* — Michael McCullough
*Assistant Examiner* — Michael E Butler
(74) *Attorney, Agent, or Firm* — Alston & Bird LLP

(57) ABSTRACT

The invention relates to a method of sorting submillimetric particles entrained in a fluid flowing in an axial direction of a main channel, the particles being of density different from the density of the fluid, and the method being characterized in that it implements, in a first region of the main channel, focusing of the particles along a wall (7) of the main channel (1) by means of at least one focusing device (3), and downstream from said region, collecting of particles in at least one sorting and take-off device (40) in communication with the main channel (1) via an opening such that the particles collected are selected by the take-off device as a function of the size of said particles, and in that said at least one sorting and take-off device is a recirculation chamber (40) in communication with the main channel (1) and presenting at least one recirculation zone (41) for concentrating the collected particles.

18 Claims, 11 Drawing Sheets

(56) References Cited

U.S. PATENT DOCUMENTS

| | | |
|---|---|---|
| 5,879,625 A * | 3/1999 | Roslaniec et al. .............. 422/50 |
| 6,506,609 B1 | 1/2003 | Wada et al. |
| 2003/0198523 A1 | 10/2003 | Bohm et al. |
| 2004/0072278 A1 | 4/2004 | Chou Hou-Pu et al. |
| 2006/0035386 A1 | 2/2006 | Hattori et al. |
| 2007/0039463 A1 | 2/2007 | Desmet et al. |

OTHER PUBLICATIONS

Daniel T. Chiu: "Cellular Manipulations in Microvortices"; Analytical and Bioanalytical Chemistry (2007); vol. 387; Jul. 28, 2006; pp. 17-20; XP002509764.

J.P. Shelby, D.T. Chiu; "Controlled Rotation of Biological Micro- and Nano-Particles in Microvortices"; Labchip; vol. 4; Apr. 21, 2004; pp. 168-170; XP002509765.

* cited by examiner

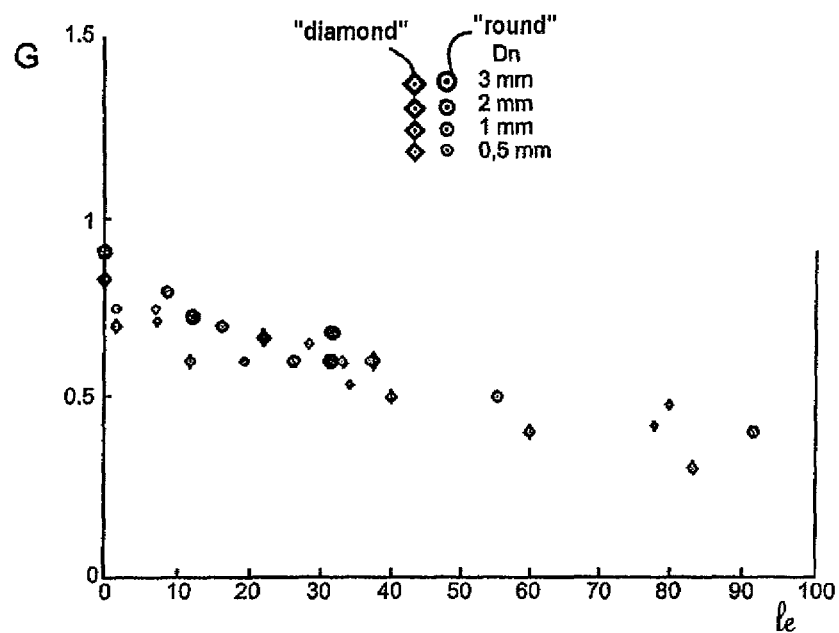
FIG.4e
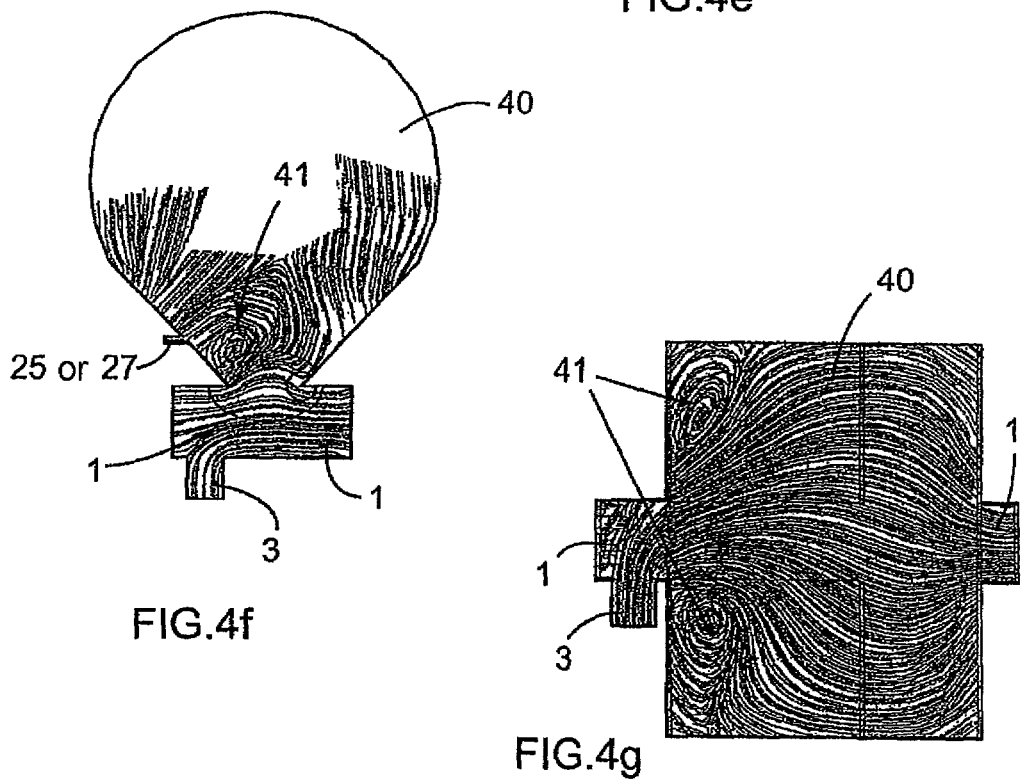
FIG.4f
FIG.4g

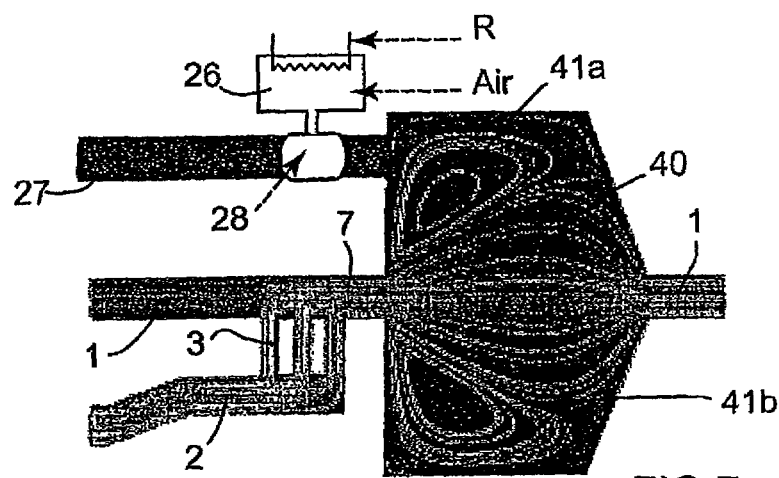
FIG.7a
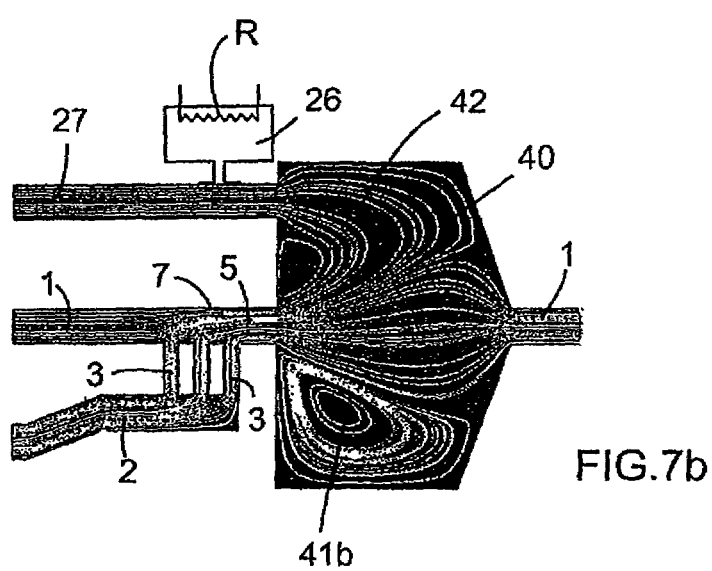
FIG.7b
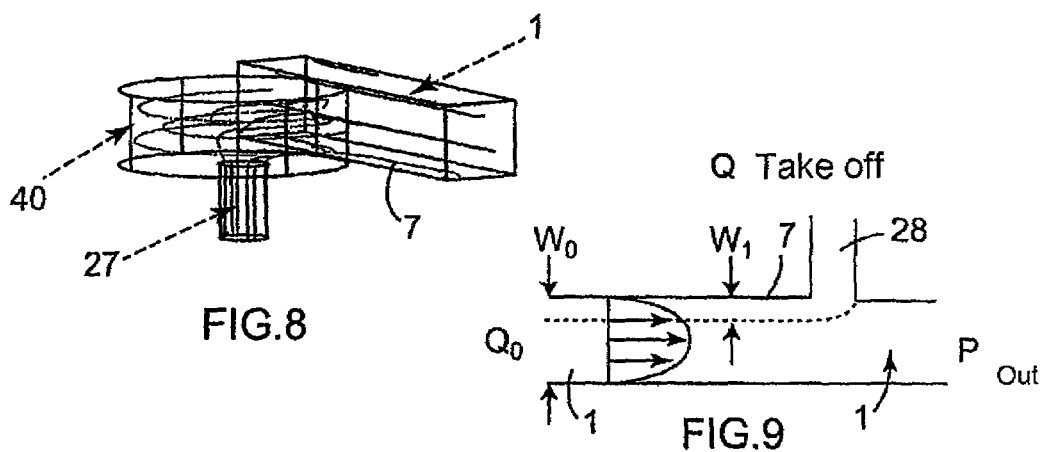
FIG.8
FIG.9

$(L+\phi)^2 = (e+\phi)^2 + Dc^2/4$
$L = \alpha Dc \; ; \; \alpha = 1.25-1.50$ → $e = \phi + \sqrt{(\alpha Dc+\phi)^2 - Dc^2/4}$

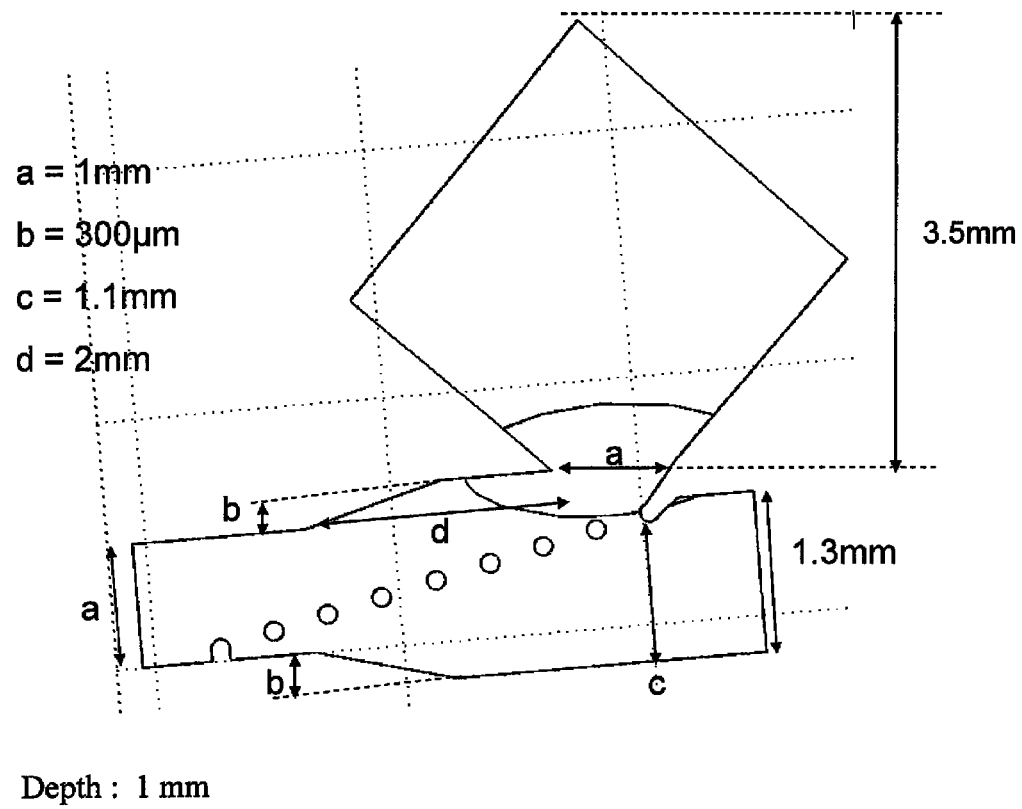
FIGURE 18A
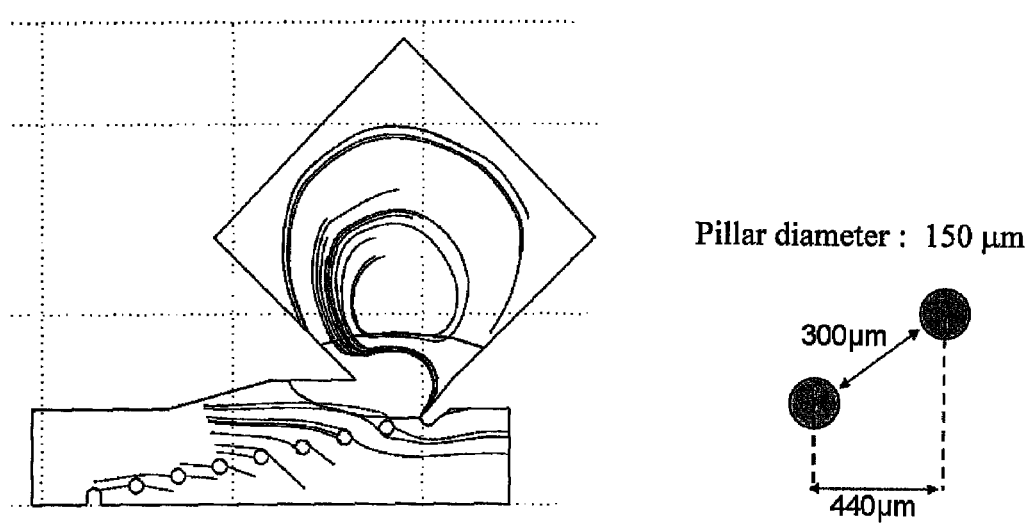
FIGURE 18B
FIGURE 19

METHOD OF SORTING PARTICLES OR PARTICLE CLUSTERS IN A FLUID FLOWING IN A CHANNEL

CROSS REFERENCE TO RELATED APPLICATIONS

This application claims priority from French Application No. 08 02577, filed May 13, 2008, which is hereby incorporated herein in its entirety by reference.

FIELD AND BACKGROUND OF THE INVENTION

The present invention relates to a method of sorting and possibly also of concentrating submillimetric particles or submillimetric particle clusters in a fluid flowing in a main channel.

Methods are already known for passive hydrodynamic sorting downstream from a periodic array of obstacles that, in each row of studs, deflects all particles larger than a critical size in the same direction, which size that is determined by the geometry of the device. With the path of the larger particles thus being inclined relative to the path of the smaller particles, it is possible to separate cells as a function of their size.

Such a technique is described in particular in the following applications: WO 2004/037374 (Huang); US 2007-026381 (Huang); or indeed US 2007-059782 (Kapur).

Another passive sorting method implements two laminar flows, namely a buffer containing particles and a particle-free focusing buffer, which buffers are urged into a narrow channel prior to penetrating into a wider channel. In that method, focusing enables the particles to be positioned against the opposite wall of the channel. The focusing is performed by laterally injecting a particle-free fluid and it is encouraged by the geometrical constriction. It enables the positions of the particles relative to the wall to be made different as a function of particle size, with the enlargement of the section enabling sorting to be performed. Thus, the smallest particles have their centers of inertia at a distance x1 (very small) close to the wall of the channel on which focusing is performed, while larger particles have their centers of inertia at a distance x2 that is greater than x1.

On passing from the pinch region to the region of enlarged section, the position difference between flow lines is emphasized, and since the particles follow the flow lines on which their centers of inertia are located, enlarging the channel emphasizes the differences in position between small and large particles.

The pinching of the flow presents the drawback of exerting shear stresses on the particles when they reach the narrow channel, and above all, because of its geometry, it gives rise to the particle samples being diluted, and the technique used does not provide any remedy for that. Such a technique is described in particular in the document "Pinched flow fractionation: continuous size separation of particles utilizing a laminar flow profile in a pinched microchannel" by Masumi Yamada et al. (Analytical Chemistry, Vol. 78, No. 18, Sep. 15, 2004, pp. 5465 to 5471).

Another known technique is an active sorting method whereby the flow lines of a fluid containing particles are deflected by locally creating a low pressure zone by suction. The paths of the particles depend on the overall balance of forces applied to the particles: as a function of their weights, densities, volumes (or diameters), and speeds, and as a function of the pressure field that results from the suction, particles are either sorted or not. Such a technique is proposed in US application No. 2007/221550 (WO 2006/102258) in the name of Barton Smith and Zachary Humes.

Yet another known technique is hydrodynamic filtering, which is described in particular in the article by Masumi Yamada and Minori Seki entitled "Hydrodynamic filtration for on-chip particle concentration and classification utilizing microfluidics", The Royal Society of Chemistry, 2005, Lab Chip 2005, 5, pp. 1233 to 1239. That method implements low rate flows in lateral channels firstly for concentrating and aligning the particles, and secondly for selecting them. Particle concentration along the walls requires a large number of lateral channels of low flow rate and of very accurate geometrical dimensions.

It is also known to make use of microvortices to trap small fluorescent particles (with size of micrometer order). That technique is described by D. Lim et al. in "Dynamic formation of ring-shape patterns of colloidal particles in microfluidic systems", Applied Physics Letters 2003, 83 (6), pp. 1145 to 1147. That method requires high-speed ranges.

A method of separating particles according to their density by centrifugal recirculation is described by Shelby et al. in "High radial acceleration in microvortices" published in Nature 2003, 425, pp. 38 et seq., for separating two types of bead having different densities (polystyrene beads with a density of 1.05 grams per cubic centimeter ($g/cm^3$) and silica beads of density in the range 1.8 $g/cm^3$ to 2 $g/cm^3$). Centrifugal recirculation serves to concentrate the low density beads in the center of the vortex and the higher density beads towards the walls of the chamber. That method requires high speeds (of the order of 20 meters per second (m/s)), together with a large difference in density between the particles. Finally, it does not enable the separated particles to be recovered.

That method therefore does not serve to sort or concentrate particles, but rather to separate particles by applying high centrifugal force (centrifugal acceleration of the order of $10^4$ meters per second per second ($m/s^2$)) with high levels of shear (of the order of $10^5$ pascals (Pa)) in the recirculation zones.

SUMMARY OF THE INVENTION

An object of the present invention is to provide a method of sorting, taking off, and optionally concentrating particles or particle clusters according to their size without necessarily requiring the solution to be diluted, and without implementing high levels of centrifugal force and/or shear.

The method of sorting submillimetric particles entrained in a fluid flowing in an axial direction of a main channel, the particles being of density different from that of the fluid, is characterized in that it implements, in a first region of the main channel, focusing of the particles along a wall of the main channel by means of at least one focusing device, and downstream from said region, sorting of particles in at least one sorting and take-off device in communication with the main channel via an opening, and in such a manner that collected particles are sorted by the sorting and take-off device as a function of the sizes of said particles, and in that said at least one sorting and take-off device is a recirculation chamber in communication with the main channel and presenting at least one recirculation zone for concentrating the collected particles.

The method thus enables the particles to be sorted by combining particle focusing with a sorting and take-off device, entry of a particle into a sorting and take-off device being conditioned by the geometrical characteristics thereof.

In addition, when the sorting and take-off device is a recirculation chamber containing a recirculation zone, the method enables the sorted particles to be concentrated prior to them being taken off.

Advantageously, said recirculation chamber may further comprise sequential take-off means, which means may be constituted by a take-off channel opening out into the recirculation chamber and preferably into the recirculation zone, thereby enabling particle concentrations to be taken off sequentially.

Preferably, said focusing is performed without pinching the flow in a region of substantially constant section of the main channel, by injecting into the main channel a fluid from a said focusing device presenting at least one lateral channel at an angle of incidence α of not less than 5° and possibly of as much as 90° to focus the particles on a wall of the channel downstream from the region where the lateral injection is performed.

Injection from a lateral channel opening out into the main channel, without constriction thereof, makes it easy to focus particles along the opposite wall without imposing harmful shear stresses to the particles.

Opposite from the injection region and facing it and/or downstream therefrom, fluid take-off may be provided via at least one fluid take-off channel, advantageously of dimensions smaller than the size of the finest particles flowing in the main channel. This can serve to solve the dilution problem.

Said at least one recirculation zone may exist in a recirculation cavity or chamber, e.g. of pseudo-rectangular, circular, or polygonal shape, having an opening that is in communication with the main channel.

Said or each recirculation chamber may be an enlarged region on either side of the main channel over a given length. The enlarged region advantageously presents an upstream wall that is substantially perpendicular to the flow axis of the fluid in the main channel.

It is thus possible to perform the concentration function with low levels of shear, since in the recirculation chambers, the fluid flows at low speed (in particular at a speed of lying in the range 5 micrometers per second (μm/s) to 1000 μm/s for a mean speed in the main channel lying in the range 1 millimeter per second (mm/s) to 50 mm/s), which is particularly advantageous with biological objects that are fragile and that present little cohesion, in particular cell clusters, and more particularly Langerhans' islets.

A plurality of sorting and take-off devices may be placed in cascade so as to collect particles of increasing sizes.

At least one additional focusing device may be placed between two of said sorting and take-off devices in cascade.

The dimensions of the openings of each of the sorting and take-off devices enable particles or particle clusters for taking off to be collected as a function of the positions of their flow lines downstream from the focusing stage, where said positions depend on their sizes.

Said at least one recirculation chamber or transverse channel may be coupled with a continuous leakage pumping channel operating at a rate that lies in particular in the range 0.1 microliters per hour (μL/h) to 500 μL/h. Advantageously, the continuous leakage pumping channel does not enable particles to be taken off, but serves to pump the fluid from the recirculation zones. The purpose is not to take off the particles from the chamber in question, but to pump out the fluid present in said chamber.

The flow rate of said leakage pumping channel may be adjustable, thereby enabling the flow lines that penetrate into a recirculation chamber to be modified, thus making it possible to select the size of the particles that enter said chamber. This variation in flow rate thus constitutes an additional parameter for adjusting the method.

In order to take off the particles that have been concentrated in a recirculation chamber, at least one particle take-off channel may be coupled to at least one recirculation chamber, particle take-off being performed sequentially, at a low flow rate, of the order of a few microliters per minute (μL/min) to a few μL/h, depending on the level of shear that the particles or particle clusters can withstand.

The method may also be characterized in that it includes at least one row of pillars, the row being inclined relative to the axis of the main channel and extending between said wall of the main channel along which said focusing takes place and the opposite wall, in order to deflect particles of diameter greater than a given diameter Dc, and including a recirculation chamber that opens out into said opposite wall of the main channel in the vicinity of the row of pillars, and upstream therefrom.

A row of pillars may be placed downstream from a focusing device and between the focusing device and a recirculation chamber and/or between two recirculation chambers.

The invention also provides a device for sorting particles entrained in a fluid circulating in an axial direction of a main channel, the device being characterized in that, in a first region of the main channel that is of substantially constant section, it includes at least one focusing device for focusing the particles along a wall of the main channel, and a second region situated downstream from said first region and presenting at least one take-off device, said at least one focusing device presenting at least one lateral channel for fluid injection and said at least one take-off device forming a recirculation chamber in communication with the main channel and presenting at least one recirculation zone for concentrating the collected particles.

BRIEF DESCRIPTION OF THE DRAWINGS

Other characteristics and advantages of the invention appear on reading the following description in association with the drawings, in which:

FIGS. 7a and 7b show a device of the invention having a recirculation zone in a recirculation cavity that is in the form of an enlarged region associated with a device for taking off particles sequentially, shown respectively in the closed position and in the open position;

FIG. 8 shows an embodiment of a device for taking particles off sequentially from a recirculation zone;

FIGS. 9 to 11 show particles being sorted by size as a function of the take-off flow rate via a transverse channel;

FIG. 18a shows an exemplary embodiment of the device of FIG. 17, dimensions included.

FIG. 18b shows a variant embodiment of the device of FIG. 17, in which the main flow channel is widened upstream a recirculation chamber.

FIG. 19 shows a dimensioned sketch for these pillars of a possible diffusion, localization and dissipation (DLD) device.

MORE DETAILED DESCRIPTION

The invention thus enables submillimetric particles entrained by a fluid in a main channel to be focused, to be sorted, and to be taken off.

The invention also makes it possible to concentrate such particles before taking them off.

Sorting is performed with the help of a channel or a chamber that communicates with the main channel via an opening that is dimensioned as a function of the sorting to be performed.

Figure 10:
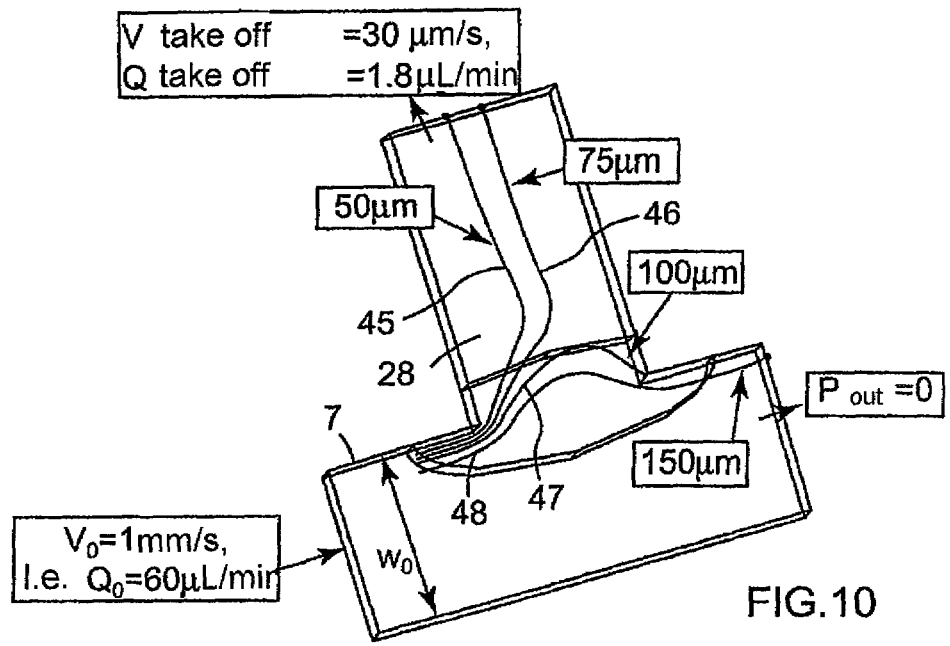

The description below shows various sorting and take-off devices in three main embodiments;
  sorting and concentration by a recirculation chamber in communication with the main channel, with particles being taken off sequentially (FIGS. 3a to 3c, 4a to 4d, 4g, 5, 6, and 8);
  sorting and concentration by a recirculation chamber having a fixed or variable leakage rate, together with sequential particle take-off; the leakage rate and the size of the opening in communication with the main channel determine the size of the sorted particles (FIGS. 4f and 12);
  sorting by a so-called "transverse" channel communicating with the central channel, the transverse channel having continuous take-off means operating at a fixed or variable take-off rate, the take-off rate and the inlet diameter of the transverse channel determining the size of the sorted particles; this embodiment does not enable particles to be concentrated, but only to be sorted and taken off (FIGS. 9 to 11); and
  sorting by means of a so-called "transverse" channel communicating with the central channel, the transverse channel having sequential take-off means 27 for operating at a fixed or variable take-off rate, together with leakage pumping means 25, the take-off and leakage rate and the inlet diameter of the transverse channel determining the size of the sorted particles; this embodiment does not enable particles to be concentrated, but only to be sorted and taken off.

Figure 1:
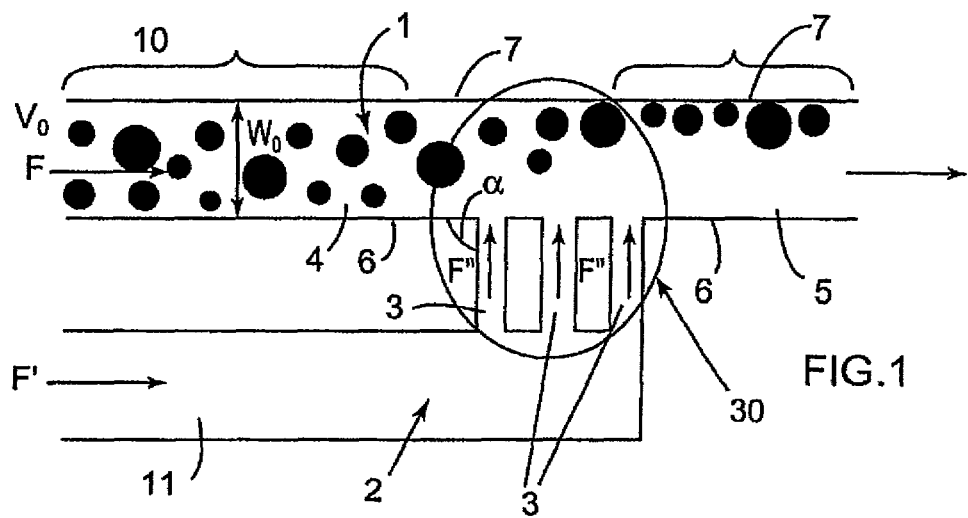
FIG. 1 shows hydrodynamic focusing of particles towards a wall in accordance with the invention.

In FIG. 1 ($\alpha=90°$), a solution of particles 10 for sorting flows in the direction of arrow F along a main channel 1 of substantially constant section with a mean flow speed $V_0$. The main channel 1 is preferably of square or rectangular section of width $w_0$ and of depth p.

A focusing solution is injected in the direction of arrow F' into an auxiliary channel 2 that opens out via one or more lateral channels 3 to perform lateral injection in the direction of arrows F", preferably perpendicularly to the direction of the arrow F. It is also possible to select an angle of incidence $\alpha$ into the flow direction in the main channel 1, where $\alpha$ lies in the range 5° to 90°.

The effect of this lateral injection is to cause the particles 10 that are distributed randomly in the main channel 1 in the upstream region 4 to be deflected in a focusing zone 30 onto the wall 7 so as to be focused in the downstream region of the main channel, which region is opposite from the wall 6 through which the lateral injection takes place.

Figure 2A:
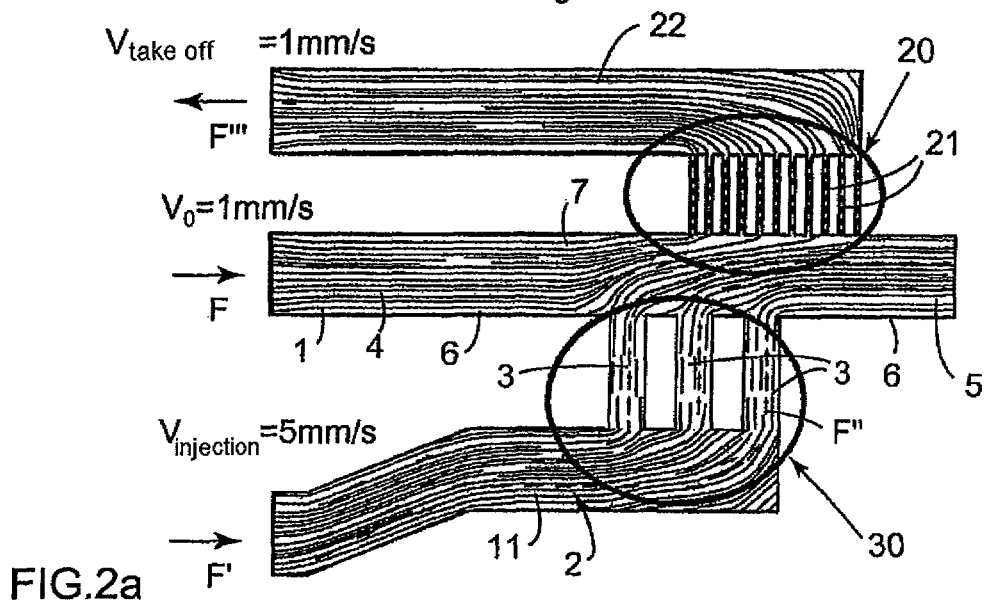
FIGS. 2a and 2b show such hydrodynamic focusing of the invention associated with fluid take-off.

It is possible to implement other ways of focusing particles on the walls, in particular it is possible to implement a focusing system based on a principle relying both on injection and on fluid take-off, as shown in FIG. 2a. In this system, in a fluid take-off zone 20, fluid take-off channels 21 open out into a fluid take-off channel 22 and are sufficiently small to prevent any particles from penetrating into these transverse channels.

The main advantage of this focusing system compared with that shown in FIG. 1 is that it enables a fluid take-off rate to be imposed to counter the dilution effect due to focusing by injection. Furthermore, by placing the channels 21 facing and/or immediately downstream from the injection zone 30, it enables the focusing of the particles on the walls to be improved while limiting the speed required for the fluid at the entry to the injection focusing system. The combination of two elements thus serves to diminish both the dilution and the shear forces applied on the particles in the focusing zone.

In the example of FIG. 2a, the take-off flow rate $Q_{take-off}$ (arrow F''') may be the same as the injection flow rate $Q_{injection}$ in order to limit or eliminate the dilution effect produced by the injection. $V_{injection}$ and $V_{take-off}$ specify the mean speeds respectively of the injection and the take-off fluids.

Figure 2B:
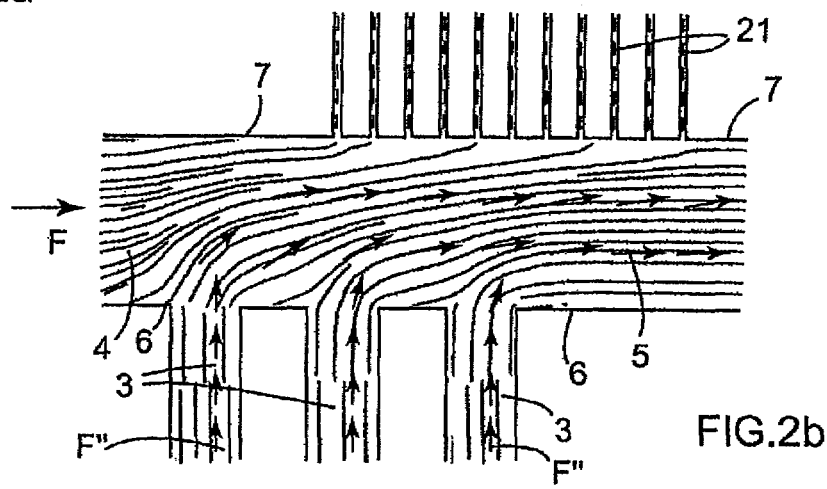

FIG. 2b is an enlargement of a detail of FIG. 2a showing how the flow lines of the fluid containing the particles for sorting are well focused on the wall.

The injected fluid that acts as a focusing buffer may be the same as the fluid containing the particles for sorting. This condition is not in any way essential, and it is entirely possible to use two different buffers, preferably buffers that are miscible.

Following this focusing stage, the particles flow in the fluid in laminar manner, being sorted according to their diameter:
  the smaller particles lie on flow lines that are very close to the wall and they can be deflected towards recirculation zones; and
  the larger particles have their centers of gravity further away from the walls, and as a result they follow flow lines that are different from those followed by the smaller particles, tracking the fluid flow in a continuous and laminar stream.

This leads to small and large particles being distributed depending on flow line position, with the positioning of particles on the flow lines depending on their centers of inertia and thus on their sizes in a flow that is laminar.

In order to obtain effective sorting, it is appropriate to accentuate the difference in position between the flow lines of small particles and large particles.

In the prior art, it is known to accentuate the position difference by a sudden enlargement of the main channel or by localized sucking out or pumping of the fluid, with the fluid-removal possibility being as described in application WO 2006/102258.

The sorting means described in that application are not configurable. In addition, there is no description of any combination with concentration means.

One of the original features of the present invention lies in placing one or more recirculation chambers downstream from the focusing stage, these chambers being accessible to particles as a function of their sizes, thereby enabling particles to be sorted by their size, and enabling said sorted particles to be taken off, while possibly also enabling them to be concentrated. Particles can be concentrated by being accumulated in at least one recirculation zone, in which speeds and thus shear forces are small.

The article by Shelby et al. (see above) shows particles being concentrated for shear stresses of the order of $10^5$ Pa by centrifugal acceleration in a recirculation chamber, the acceleration being of the order of $10^4$ m/s$^2$. Such orders of magnitude are not compatible with manipulating particles or clusters of particles that are fragile, such as Langerhans' islets. A device of the invention enables recirculation zones to be obtained and thus enables concentration to be obtained with shear rates of the order of 5 Pa, since it does not operate at all by implementing centrifugal force in order to separate and concentrate particles. By way of example, the centrifugal accelerations are of the order of $10^{-5}$ m/s$^2$ in the present invention. The invention can therefore be used advantageously for manipulating and concentrating particles or clusters of particles that are fragile, such as Langerhans' islets.

Figure 3A:
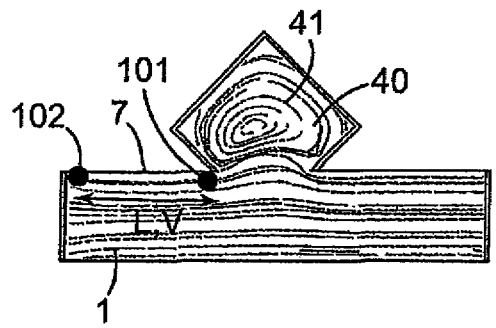
FIGS. 3a to 3c show the implementation of a recirculation zone in the form of a closed cavity in accordance with the invention, with FIGS. 4a to 4d showing example shapes for the cavity, FIG. 4e plotting the limiting Reynolds number Re for obtaining recirculation with various chamber diameters, and FIGS. 4f and 4g showing the recirculation flow lines in a cylindrical chamber and a rectangular chamber, respectively.
Figure 3B:
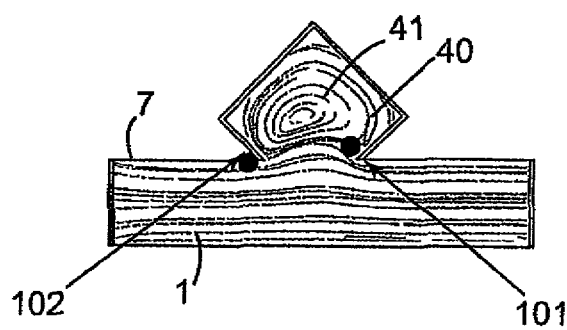
Figure 3C:
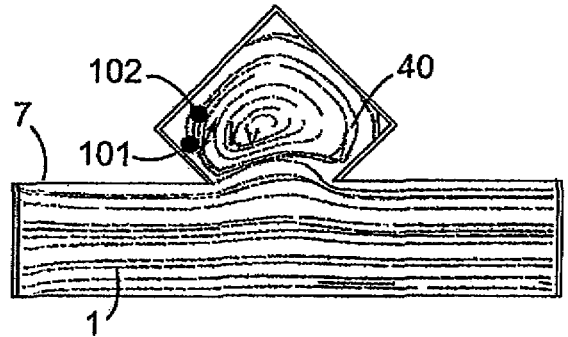
Figure 4A:
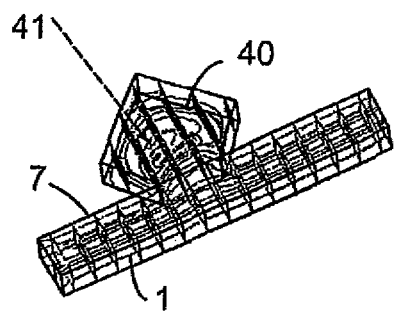

As shown in the state of the art, dilution is a major drawback in most existing hydrodynamic sorting techniques. To solve that problem, use is made of the concentrating power of recirculation zones. As shown in FIGS. 3a to 3c, the separating power of such recirculation chambers 40 comes from the large speed differences that exist between the main channel and the recirculation zone, which difference is strongly dependent on the shape of the chamber.

Consideration is given to two particles 101 and 102 that are traveling at a speed V and that are separated by a distance L in the main channel 1, and at a speed $\underline{v}$ and that are separated by a distance l in the recirculation chamber 40.

In the main channel, the two particles are separated by:

$$\tau = \frac{L}{V}$$

In the cavity, the two particles are separated by:

$$\tau = \frac{l}{v}$$

Thus, when both particles are in the cavity:

$$l = \frac{v}{V}L$$

Since v<V, l<L. The effect of the cavity is thus to move the particles closer together, which amounts to concentrating them.

Figure 4B:
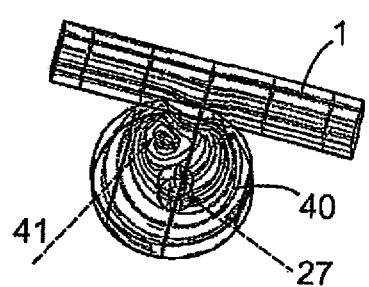

Various shapes may be used for inducing recirculation zones 40, amongst which mention can be made of chambers:
  that are polygonal, e.g. lozenge-shaped ("diamonds") (FIG. 4a), or pseudo-rectangular or rectangular, and in particular trapezoidal (of the type shown in FIGS. 4c and 4d); and
  that are circular, in particular cylindrical (FIG. 4b).

In FIG. 4b, reference 27 corresponds to a particle take-off channel that is described below.

With fragile particle clusters, modeling has shown that the speeds needed for obtaining usable recirculation zones are particularly low in chambers of circular or polygonal shapes that communicate with the main channel via a calibrated opening. It is thus this type of shape (cf. FIG. 4a or 4b) that is recommended when it is desired to sort, concentrate, and take off fragile particle clusters presenting little cohesion, such as Langerhans' islets.

In each chamber, recirculation zones 41 can be obtained beyond a limiting Reynolds number that depends in particular:
  on the shape of the chamber (opening into the cavity, depth, etc. . . . );
  on the maximum speed in the main channel; and
  on the shape of the main channel (in particular its depth).
Reynolds number Re is expressed as follows:

$$Re = \frac{V_1 L}{\upsilon}$$

with:
  $V_1$: maximum speed of the fluid in meters per second (m/s);
  L: the characteristic dimension of the shape under consideration in meters (m); and
  $\upsilon$: dynamic viscosity of the fluid in square meters per second (m$^2$/s).

G is defined as the ratio between the depth of the chamber and the length $D_h$ of its opening. FIG. 4e shows examples of the value of the Reynolds number Re as a function of the ratio G for water or an aqueous buffer, for various values of $D_h$ lying in the range 0.5 millimeters (mm) (for a small chamber) to 3 mm (for a chamber said to be of "large dimensions") of round and in particular of cylindrical shape or of lozenge-shape ("diamonds").

Figure 4C:
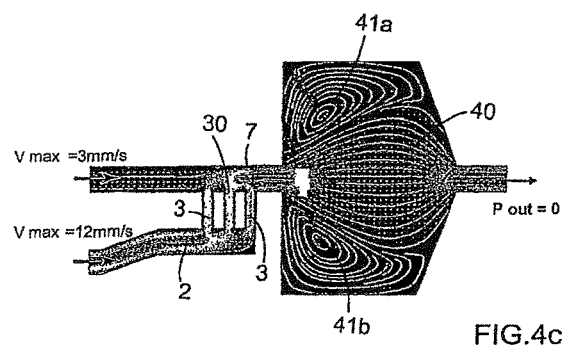

FIG. 4c shows the principle of the invention combining the system for focusing particles on the wall with concentration zones 41a and 41b for certain particles in recirculation chambers 40, here of pseudo-rectangular shape, extending on both sides of the main channel 1. It will be understood that only certain particles flowing along certain flow lines participate in the recirculation zone 41a, and are thus concentrated. These are particles moving along the flow lines closest to the wall 7, corresponding to the smallest-diameter particles. Only the zone 41a contains sorted particles and is thus used by the method.

Figure 4D:
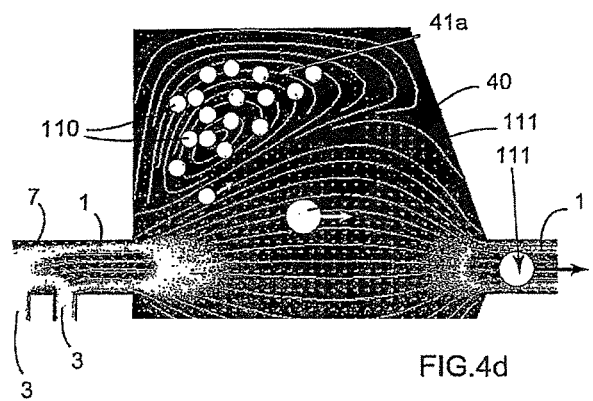

FIG. 4d shows the principle of the sorting microsystem: by following the flow lines that are very close to the wall, the smallest particles 110 move towards the recirculation zone 41a. They are attracted towards the center of recirculation zones 41a by various forces, including above all Stokes' hydrodynamic drag, inertia, and gravity.

The larger particles 111, i.e. those further away from the wall, continue on their path and exit downstream from the recirculation chamber 40.

FIGS. 4f and 4g show the flow lines in greater detail inside and outside a circular recirculation zone of diameter 5 mm (FIG. 4f) with a mean entry speed of 1 mm/s (focusing speed 1 mm/s), for an imposed mean speed of 2 mm/s in the main channel and a speed of the order of 5 μm/s in the center of the cavity, and a rectangular recirculation zone (FIG. 4g) with an entry speed of 1 mm/s and a speed at the inlet orifice of the cavity of 50 mm/s (mean focusing speed: 50 mm/s). The calculated speeds in the recirculation zones 41 are thus of the order of a few tens to a few hundreds of µm/s, and the maximum shear speeds are of the order of 2.5 mm/s for a circular chamber, and 60 mm/s for a rectangular chamber. It should be observed that the recirculation chamber shown in FIG. 4f has a leakage channel 25, with a leakage rate that is 160 µL/h.

It should be observed that the characteristics of the openings of the cavities make it possible to deflect the flow lines that are closest to the wall 7 opposite from the focusing system, these flow lines corresponding to a certain particle diameter as a result of the focusing performed upstream.

More precisely, if Dc is the maximum diameter of particles to be taken off, it is possible to define the characteristics of the openings of the cavities so as to capture flow lines situated at a distance Dc/2 relative to the wall 7 corresponding to particles of radius smaller than or close to Dc/2. These characteristics can be defined by modeling performed using appropriate software, e.g. Comsol software well known to the person skilled in the art. The parameters of the model are the dimensions of the chamber(s), of the main channel, the nature of the fluid (in particular its dynamic viscosity), and the flow rates or pressures imposed at the inlets and outlets of the various channels.

Such software can also be used to model the flow lines in the recirculation zones, thus making it possible to adjust the above-mentioned parameters, e.g. for the purpose of optimizing the concentrating power obtained by such zones.

Figure 6:
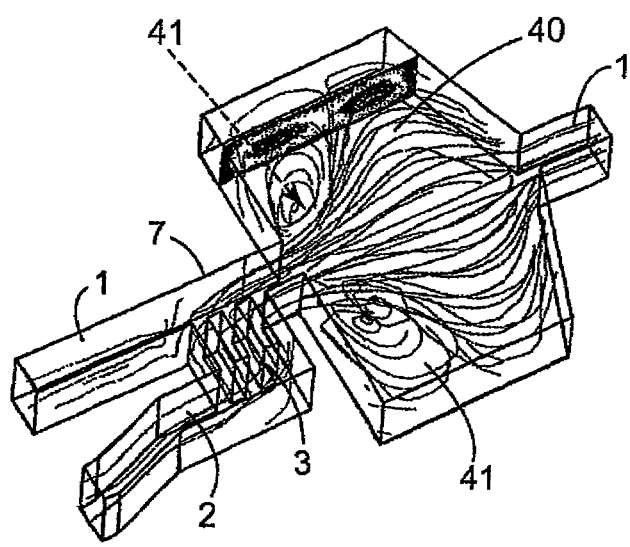
FIG. 6 shows a recirculation zone implemented in the form of an enlarged region of the main channel.

FIG. 6 shows a model of the flow lines in a microsystem having a depth of 1 mm, comprising a focusing stage preceding a pseudo-rectangular chamber. This figure illustrates the concentrating power by comparing the characteristic speeds in the main channel 1 ($V_{max}$=50 mm/s after focusing) and the level of recirculation 41 ($V_{max}$ of the order of 0.5 mm/s to 1 mm/s depending on position within the recirculation). The appearance or non-appearance of recirculation downstream from focusing can thus be modeled, as mentioned above.

By placing various cavities 40 in cascade one after another, it is possible to sort, trap, and concentrate in each chamber particles of different sizes. In the particular circumstance where the size and the number of cavities connected in cascade are large, it may be appropriate to add a focusing system between two cavities in order to ensure that the particles are indeed situated against the wall and can penetrate into the concentration cavity.

Figure 5:
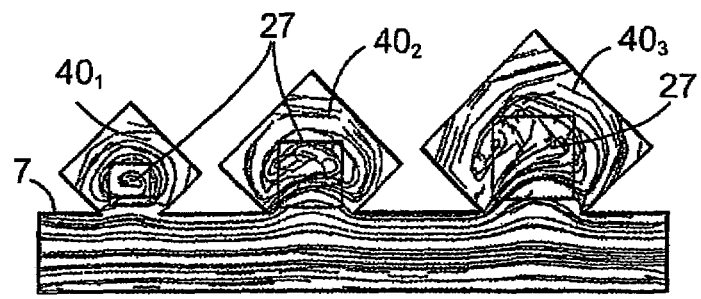
FIG. 5 shows three lozenge-shaped cavities implemented in cascade.

FIG. 5 is a plan view of three lozenge-shaped cavities 40₁, 40₂, and 40₃ that are placed in cascade. The squares shown in the centers of these cavities correspond to particle take-off channels 27 that are described below. By way of example, in the main channel the maximum speed is 1.9 mm/s and in each of the cavities 40₁ to 40₃ it is of the order of 70 µm/s (values spread from 5 µm/s to 70 µm/s). A very clear speed difference between the main channel 1 and the cavities 40₁ to 40₃ enables the particles to be concentrated.

Under such circumstances, particle selection by size as performed by the openings of the cavities takes place in increasing order: the smallest particles are collected by the cavity 40₁, particles that are slightly larger are collected by the cavity 40₂, etc. . . . .

Particle Take-Off System

The invention also includes a take-off system enabling the particles that have accumulated in the recirculation chambers 40 to be recovered.

This take-off is sequential from a take-off channel 27 controlled by a fluidic valve 26. When the valve is closed (FIG. 7a), particles accumulate in the recirculation zones 41a and 41b of the chambers 40 in which recirculation is taking place. Once the particles are concentrated, the valve 26 is opened (FIG. 7b) and the flow lines are deflected as a result of the valve 26 opening, thereby enabling the particles that have been sorted and concentrated to be recovered in the channel 27.

As shown, it is possible for example to use a fluidic valve 26 that is opened and closed under temperature control: while the air is maintained at ambient temperature, the valve 26 is open and take-off is performed by eliminating the circulation 41 and forming a flow 42. By increasing the temperature of the air contained in the chamber (by means of a heater resistance R), the pressure of the gas contained in the chamber is raised. The gas 28 then penetrates into the channel 25 and blocks the flow of fluid.

The embodiment shown in FIG. 8 implements a take-off channel 27 (see also FIG. 4b) at the center of a closed cavity 40, e.g. a circular cavity, for concentrating particles. The flow rate in the take-off channel 27 is small (a few (µL/min) to a few µL/h).

Passive Sort/Concentration Coupling with Pillars

In another embodiment, the invention implements a sorting system coupled to recirculation zones with coupling that is also purely passive in the sense that it is only the shape of the device that causes particles to penetrate into the recirculation zones.

This configuration is preferred for large clusters of cells, such as Langerhans' islets.

The operation of the device comprises two steps: firstly the particles are focused on the wall 7 opposite from the recirculation chamber, as described above. Sorting is then performed by a row 60 of pillars 50 forming a determined angle β relative to the axis of the main channel 1. The geometrical characteristics of the pillars 50 of diameter Φ are such that particles smaller than a critical size Dc are generally not deflected since they go past the obstacle constituted by the row of pillars 50, whereas particles larger than the critical size Dc are deflected at each row of pillars, and always in the same direction, towards the recirculation chamber 40. Under such circumstances, it should be observed that the recirculation chamber is preferably located on the wall opposite from the wall 7, i.e. on the same side as the focusing device. This device enables sorting to be performed by decreasing size.

The row 60 of pillars 50 in this device enables sorting to be performed by size by deflecting particles according to their size, as described for example by Huang in "Continuous particle separation through deterministic lateral displacement" published in Science 2004, 304, pp. 987 to 990, with the difference that only one row of pillars is used instead of an array of pillars, where this is made possible by the prior focusing of the particles along the wall 7. This makes it possible to ensure that particles of selected size penetrate into the recirculation zones: the steric hindrance effect of a pillar is such that the pillar causes the particle to change flow line, thereby forcing it to penetrate into a recirculation zone.

When the device includes such a row of pillars enabling sorting to be performed by size, using a device of the diffusion, localization, and dissipation (DLD) type, it is preferably situated downstream from the focusing. However it is also possible to imagine such a row of pillars without providing a focusing stage upstream. Under such circumstances, the row performs both the focusing function and the size sorting function.

Dimensioning is based essentially on the morphology of the flow lines.

Figure 13:
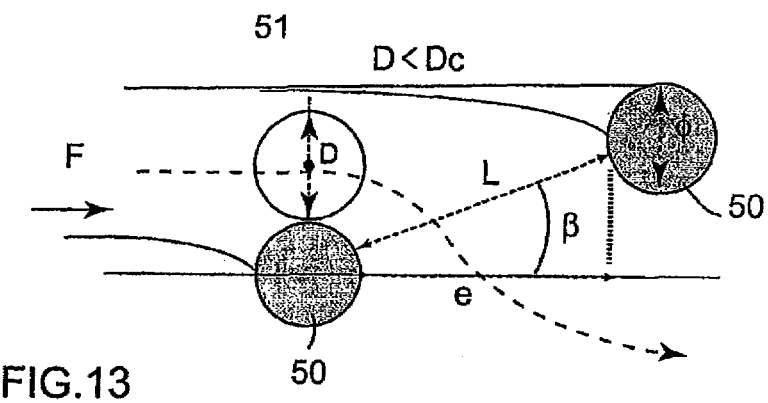
FIGS. 13 to 17 show particles being sorted by size and with the help of a row of pillars for each particle size to be sorted.

When speed of a particle is low (i.e. when its inertia is negligible), a particle of small size (diameter less than Dc) follows the flow line passing through its center of gravity (FIG. 13) such as for example the particle 51 of diameter less than Dc.

Figure 14:
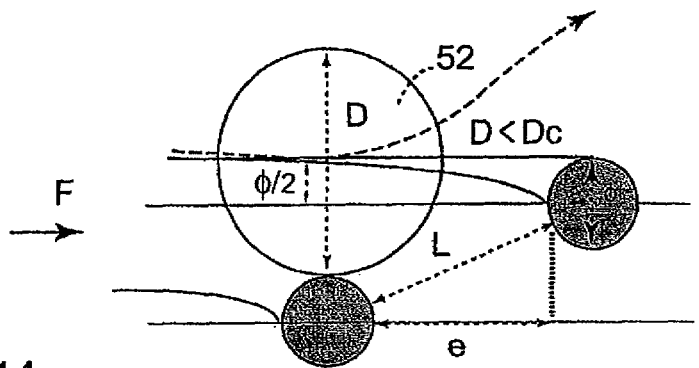

In contrast, a particle of diameter greater than or equal to Dc is deflected by the row of pillars, due to steric hindrance. The row of pillars thus deflects its flow line (cf. FIG. 14) in the manner shown for the particle 52 of diameter greater than Dc.

Figure 15:
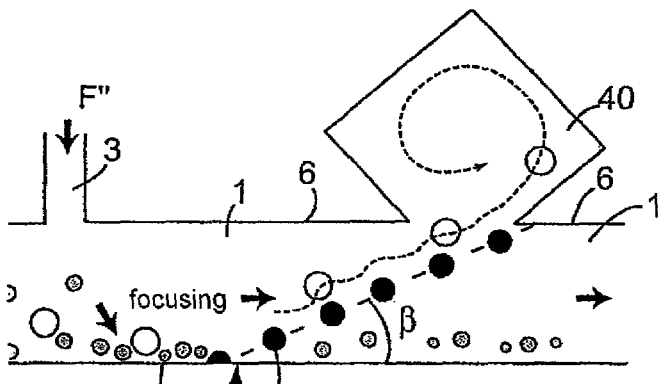

In summary, particles smaller than the critical size Dc continue on their path within the channel 1, while the other particles are pushed into the recirculation zone by the row of pillars 50 having its axis inclined at an angle β relative to the flow direction F, and the particles are accumulated therein (cf. FIG. 15). It should be observed that a row 60 of pillars may be placed between two recirculation chambers 40 with or without a focusing device being interposed, thereby making it possible to perform sorting on decreasing sizes. Since the largest particles are the easiest to deflect, the cavities located downstream from the pillars will preferentially collect the particles that have been deflected, i.e. the largest particles.

Figure 16:
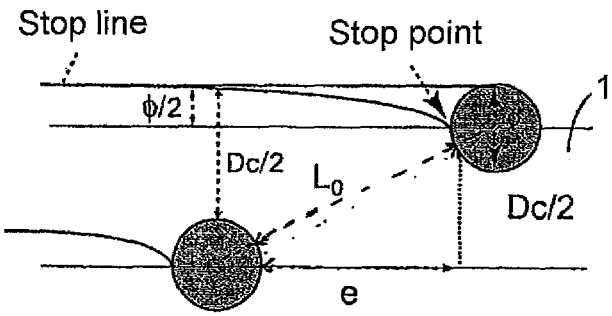

The dimensioning of this system is given by the diagram of FIG. 16.

The flow lines that terminate on the pillars 50 (cf. stop point) are the critical lines that steer the particles:
- either towards the outlet of the main channel, i.e. the particles pass through the row 60 of pillars 50 without being deflected; or
- else towards the recirculation chambers 40, with the particle being deflected on each pillar 50 because of steric hindrance.

These critical lines are not strictly parallel to the axis of the channel and it can be estimated that at a distance of a few hundred micrometers from the pillar, the critical line is situated at a distance $\Phi/2$ from the horizontal line passing through the center of the pillar of diameter $\Phi$. This imposes transverse spacing between pairs of pillars of the order of Dc/2.

The axial spacing (e+Φ) between the centers of two pillars 50 is given by applying Pythagoras' theorem:

$$(L_0\Phi)^2 = (e+\Phi)^2 + Dc^2/4$$

Since the distance $L_0$ between pairs of pillars needs to be large enough to avoid constituting a filter, there is an additional condition:

$$L_0 \geq aDc \text{ with } a \approx 1.25 \text{ to } 1.50$$

The axial spacing e between the pillars 50 is deduced as follows:

$$e = -\Phi + \sqrt{[(aDc+\Phi)^2 - Dc^2/4]}$$

$$\cos \beta = (e+\Phi)/(L_0+\Phi)$$

and with Φ, e, and $L_0$ are imposed, so β is determined.

Figure 17:
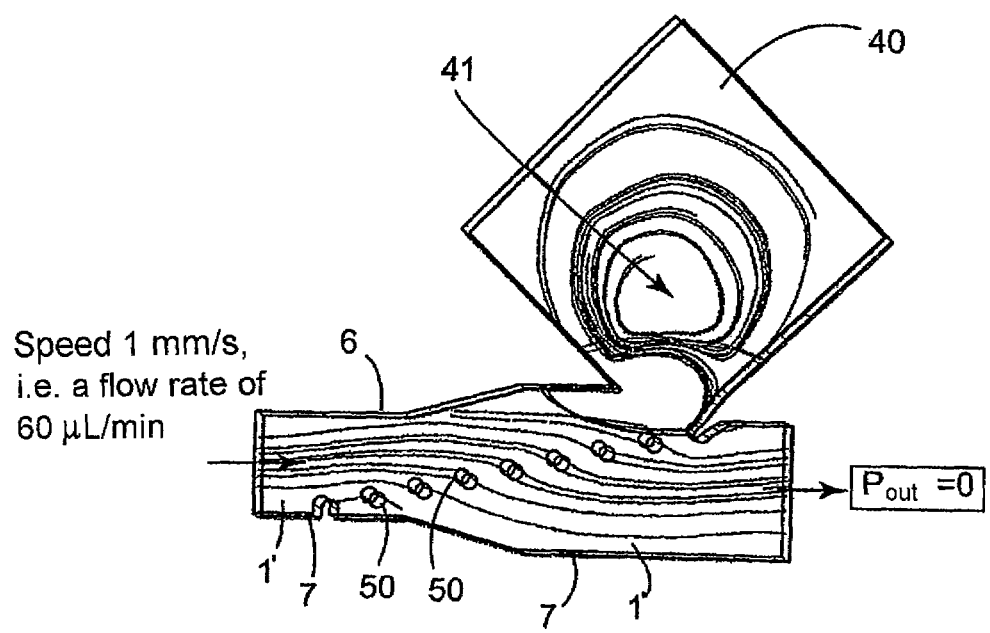

FIG. 17 is an overall view of a sorting and recirculation device implementing a row 60 of pillars 50 while also enlarging the main channel 1' at the row 60 of pillars 50.

In FIG. 17, it can be seen that the main channel upstream the recirculation zone is asymmetrical, such a shape making it possible to adjust the radii of curvature of the field lines at the entrance to each recirculation zone. The radii of curvature can thus be arranged in such a manner that the particles moving on the field lines are extracted from their field lines by inertia by the radius of curvature (cf. FIG. 17). Such asymmetry is particularly useful when the particles for concentrating are of larger size. This then avoids a leakage flow being provided inside the recirculation zone. In dimensioned FIG. 18a, such asymmetry is shown, the main channel being progressively widened, so as to form a recess upstream the recirculation chamber. Whereas FIG. 18a shows the main channel being also widened opposite to the input of the recirculation chamber, FIG. 18b shows another way to widen the main channel upstream the recirculation chamber, with only one recess just near the input of the recirculation case.

In FIGS. 17, 18a and 18b, a device of the diffusion, localization, and dissipation (DLD) type is situated upstream the recirculation zone, so as to ensure that particles of selected size penetrate into the recirculation zones. Although of significant interest, such device is not compulsory.

In FIG. 19, details regarding a possible diffusion, localization and dissipation (DLD) type are provided. This particular case mainly fits with particles being 200 μm in diameter.

Although not displayed in FIGS. 17, 18a and 18b, a focusing device, as previously described, may be situated upstream the flow.

The recirculation chamber 40 shown in FIGS. 15 and 17 may present a take-off channel 27 so as to enable particles to be taken off after they have been concentrated (e.g. as in FIG. 7a or 7b).

Examples of Modeling a Sorting and Concentration System

Example 1: a Device for Sorting, Concentration, and Take-Off Comprising a Row of Pillars The sorting device of FIG. 17 is designed in such a manner that particles of size smaller than 200 micrometers (μm) pass through the row of pillars without being deflected overall, while particles of size greater than 200 μm are deflected on each pillar towards the recirculation chamber.

The characteristics of the proposed system were determined from the following dimensioning rules:
- critical sorting diameter: Dc=200 μm;
- pillar diameter: Φ=150 μm;
- transverse spacing between pillars: Dc/2=100 μm;
- axial spacing e+Φ=440 μm, $L_0$=300 μm.

In another embodiment, the invention implements a sorting system coupled to recirculation zones with coupling that is active, in the sense that the shape of the device coupled with leakage pumping causes particles to penetrate into the recirculation zones.

A fluid pumping device, referred to as a leakage pump, may also be provided within one or more of the recirculation chambers. Example 2 below explains the main advantage of leakage pumping which is that it is easily modulated, thereby enabling the hydrodynamic properties of the invention to be adjusted.

Example 2: Transverse-Channel Sorting and Take-Off Device

FIG. 9 shows an example in which particles are sorted by means of a transverse channel 28 that is preferably placed perpendicularly to the main channel. In this example, external continuous take-off means enable a take-off flow rate $Q_{take-off}$ to be applied through said transverse channel.

For a particle to penetrate into the transverse channel 28, it is necessary for its radius to be smaller than or close to the width $w_1$ of the stream entering the cavity (see FIG. 9). This width corresponds to the distance $w_1$ beyond which the flow lines do not penetrate into the opening: particles with their centers of inertia moving along a flow line situated beyond the distance $w_1$ from the wall 7 are not directed towards the transverse channel 28 and therefor remain in the main channel. In contrast, particles having their centers of inertia traveling along a flow line that is situated closer to the wall 7 than the distance $w_1$ are deflected towards the opening. It is therefore appropriate to speak of collection being selective relative to size. The maximum size of particle that can penetrate into the cavity is thus equal to $2w_1$.

On the basis of this consideration, integrating Purday's parabolic speed profile serves to associate the size of the sorted particles with the continuous take-off flow rate $Q_{take\text{-}off}$, where $V_{take\text{-}off}$ designates the speed of the fluid taken off:

$$\frac{Q_{take\text{-}off}}{Q_0} = \left[\frac{r+1}{r}\right]\left\{\frac{w_1}{w_0} - \frac{1}{2(r+1)}\left[1 - \left(1 - \frac{w_1}{w_0/2}\right)^{r+1}\right]\right\} \quad (1)$$

where $w_0$ is the width of the main channel, $w_1$ is the radius of the sorted particle and b is the depth of the channel, with $Q_0$ being the flow rate in the main channel 1;

r is an exponent that depends on the ratio $\alpha=w_0/b$ if $w_0 \leq b$ or $\alpha=b/w_0$ if $b \leq w_0$.

This gives r=2 for $\alpha \leq \frac{1}{3}$ and r=2+0.3 $(\alpha - \frac{1}{3})$ for $\alpha > \frac{1}{3}$.

By adjusting the continuous take-off rate, it is possible to recover and concentrate different sizes of particle in a cavity, the maximum size of particle that can penetrate into the cavity being $2w_1$. This example shows that it is possible to collect sorted particles in a transverse channel, the collection being selective to the size. It will be easily understood that this selective collection can be carried out by adjusting the geometrical parameters ($w_1$, $w_0$) as well as hydrodynamical parameters such as the continuous take off flow rate $Q_{take\text{-}off}$, the speed of the fluid taken off $V_{take\text{-}off}$, and the flow rate $Q_0$ in the main channel 1.

Explanation of the Reconfigurable Nature of the Device

The size of the sorted particles depends both on the continuous take-off rate and on shape.

For the following dimensions (FIG. 10):
main channel: 1 mm wide ($w_0$=1 mm) for a depth of 1 mm; and
transverse channel: 1 mm wide for a depth of 1 mm.
And desired sorting size of 200 µm, i.e. $w_1$=100 µm, feeding the numbers into equation (1) gives:

$$\frac{Q_{take\text{-}off}}{Q_0} = \frac{V_{take\text{-}off}}{V_0} = 0.0295$$

where $V_0$ is the mean speed of the fluid in the main channel 1. Thus, if $V_0$=1 mm/s, then $V_{take\text{-}off}$=30 µm/s.

Numerical simulations show (cf. FIG. 10) that the flow lines 45 and 46 situated respectively at 50 µm and at 75 µm from the edge 7 in the main channel 1 penetrate completely into the transverse channel 29, and that the flow line 47 situated at 100 µm from the wall 7 is at the limit of penetration. Finally, any flow line situated further than 100 µm from the wall 7 (e.g. the line 48 situated at 150 µm from the wall 7) does not penetrate into the transverse channel 29.

Consequently, for the same shape, by varying the leakage flow rate, it is possible to cause the critical sorting size to be 300 µm, where feeding the numbers into equation (1) gives:

$$\frac{Q_{take\text{-}off}}{Q_0} = \frac{V_{take\text{-}off}}{V_0} = 0.0635$$

Figure 11:
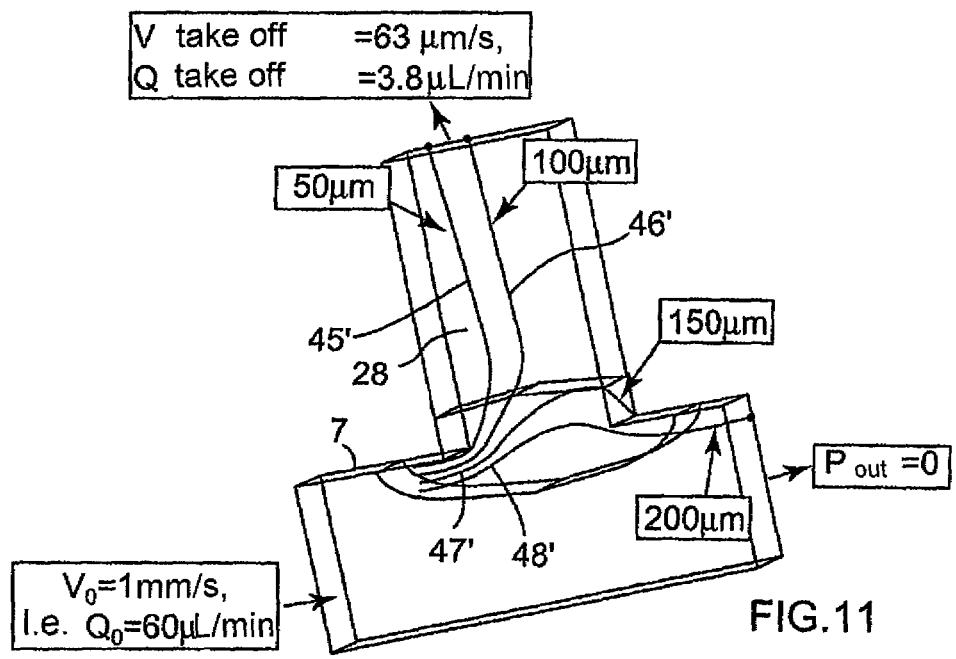

By conserving a speed of 1 mm/s at the inlet to the main channel, this requires a take-off speed of 63 µm/s. As shown by the simulation of FIG. 11, this time flow lines 45' and 46' lying respectively at 50 µm and at 100 µm from the wall 7 penetrate completely, whereas a flow line that is more than 150 µm from the wall 7, e.g. the flow line 48' situated at 200 µm therefrom, cannot penetrate into the transverse channel 29, the flow line 47' situated at a distance of 150 µm from the wall 7 being at the limit of penetration.

In the above example, the flow lines are guided by means of a channel 29 that is perpendicular to the main channel 1, with means that enable a continuous take-off rate to be applied, thereby enabling particles to be selected that are situated on the deflected flow lines, i.e. that are situated at a certain distance from the wall 7.

Example 3: Sorting, Concentrating, and Take-Off by Means of a Recirculation Chamber The same principle can be applied to other shapes, such as recirculation cavities, within which it is possible advantageously to provide external leakage pumping means 25 enabling an adjustable leakage rate to be produced, thereby imparting a reconfigurable nature to the device. The leakage pumping means is not essential, but it does constitutes an additional parameter that enables the hydrodynamic properties of the invention to be modified, given that the other parameters (dimensions, fluid viscosity, main flow rate) are not variable. Preferably, the leakage pumping is performed through a leakage pumping channel that is too narrow for particles to penetrate therein, said channel opening out into a portion of the recirculation chamber that lies outside a particle concentration zone. Such a leakage channel 25 may be associated with any recirculation chamber 40 located downstream from a focusing stage 30. A row of pillars 50 may precede the opening of said recirculation chamber.

It is thus possible to couple such a leakage channel 25 to a recirculation zone 41 in order to concentrate particles that are sorted according to size.

The example below (FIG. 12) illustrates such coupling: the device is dimensioned so that particles of diameter smaller than 200 µm ($w_1$=100 µm) penetrate into the recirculation zones 41 where they become concentrated.

The device has a focusing/sorting zone and a concentration zone in the recirculation that appears in the circular cavity having a diameter of 5 mm. The geometrical characteristics of the example given below are given as follows:
main channel 1: width 1 mm ($w_0$=1 mm) and depth 1 mm (p=1 mm);
focusing channel 3: width 500 µm and depth 1 mm;
leakage pumping channel 25: width 100 µm over a depth of 1 mm; and
cavity 40 with diameter of 5 mm.

If the following are imposed: a mean speed $V_0$ of 1 mm/s at the inlet, a focusing speed $V_{focusing}$ of 1 mm/s, and an outlet pressure equal to atmospheric pressure, then applying equation (1) indicates that the leakage speed should be 450 µm/s:

$$Q_{focusing} = V_{focusing}S = (1 \times 10^{-3})(500 \times 10^{-6})(1 \times 10^{-3})$$
$$= 0.5 \times 10^{-9} \text{ m}^3/\text{s}$$

$$Q_{main} = V_{main}S = (1 \times 10^{-3})(1 \times 10^{-3})(1 \times 10^{-3}) = 1 \times 10^{-9} \text{ m}^3/\text{s}$$

$$Q_0 = 1.5 \times 10^{-9} \text{ m}^3/\text{s}$$

With $S = w_0 \times p$ and m³/s stands for cubic meters per second.

Thus:

$$Q_{leak} = 0.03 \times Q_0 = 0.045 \times 10^{-9} = V_{leak} \times S$$

which gives:

$$V_{leak} = \frac{Q_{leak}}{(100 \times 10^{-6})(1 \times 10^{-3})} = \frac{0.045 \times 10^{-9}}{(1 \times 10^{-4})(1 \times 10^{-3})} = 0.045 \times 10^{-2} \text{ m/s} = 450 \text{ µm/s}$$

The above numerical modeling shows that:
the flow lines at 50 µm of the wall 7 after focusing do indeed penetrate into the recirculation cavity 40, while those situated at 150 µm, for example, from the wall 7 are excluded from the recirculation zones; and
the leakage pumping 25 does not eliminate the recirculation zones (cf. FIG. 4f).

Figure 12:
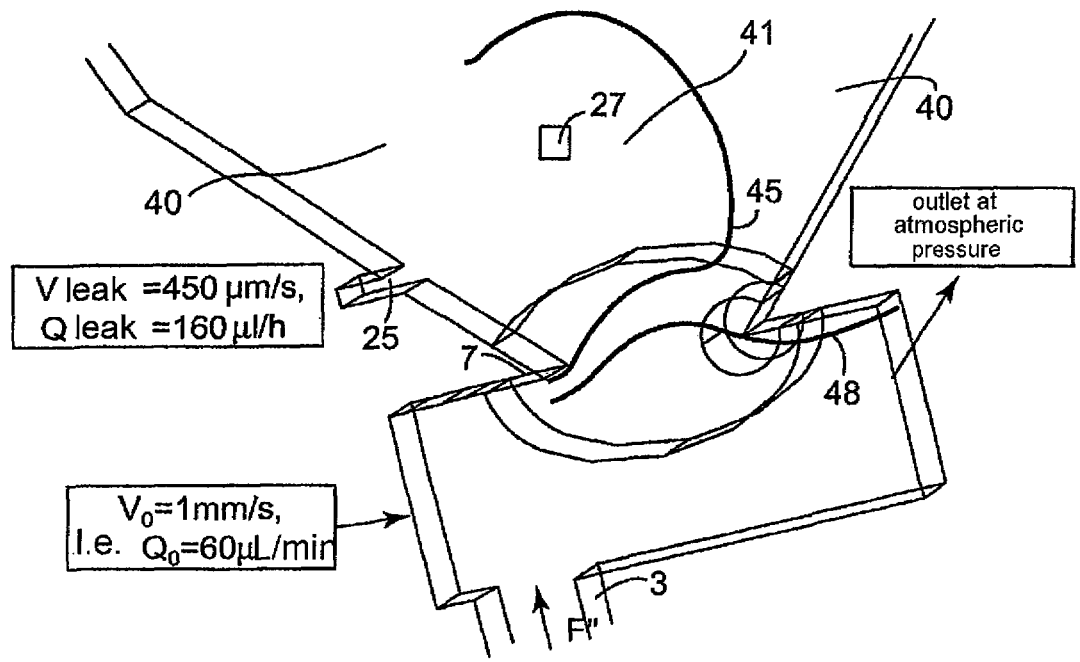
FIG. 12 shows particles being sorted by size as a function of leakage pumping rate 25, this figure corresponding to a "zoom" view of the recirculation chamber shown in FIG. 4f.

In FIG. 12, there can be seen a sequential take-off channel 27 in the middle of the recirculation zone 41.

In order to illustrate the reconfigurable nature of the invention, an example is given with reference to a circular cavity 40 (FIG. 4b or 8) of diameter 1.5 mm with $Q_0 = 15$ µL/min, a square main channel 1 with dimensions 500 µm×500 µm, and a leakage square pumping channel 25 with dimensions 300 µm×300 µm. This gives:

a) for $V_{max} = 1.8$ mm/s (maximum speed in the main channel) and $V'_{max} = 50$ µm/s (maximum speed in the cavity), then critical size $2w_1 = 100$ µm, with $Q_{leak} = 26$ µL/h;

b) with $V_{max} = 1.8$ mm/s and $V'_{max} = 14$ µm/s, then $2w_1 = 50$ µm, with $Q_{leak} = 6.9$ µL/h; and c) with $V_{max} = 1.8$ mm/s and $V'_{max} = 14$ µm/s, then $2w_1 = 10$ µm, with $Q_{leak} = 0.3$ µL/h.

The maximum speed of particles in the cavity 40 is respectively 36 times, 100 times, and 129 times smaller than the maximum speed in the main channel. It will be understood that such speeds are suitable for concentrating low-cohesion clusters of fragile cells such as Langerhans' islets.

The concept of critical size means that particles smaller than the critical size penetrate into the cavity where they become concentrated, whereas particles greater than the critical size continue along the main channel without penetrating into the cavity or else they exit therefrom.

The above example shows that with a given inlet flow rate $Q_0$ and a given shape, it is possible to vary the critical size by a factor of 10 (over the range 10 µm to 100 µm) by varying the leakage rate $Q_{leak}$.

A device of the invention is thus more flexible in use since for given geometrical characteristics, the user can perform sorting on different critical sizes. This is advantageous, in particular when compared with the technique described by M. Yamada and M. Seki (above-mentioned article published in Lab Chip 2005, pp. 1233 to 1235) in which it is necessary to adjust the fluid flow resistances of the transverse channels, or else compared with known stream-pinching techniques that do not enable the critical size to be defined.

The invention can be used to sort and concentrate particles regardless of whether they are biological or not. Thus, by adapting the dimensions of the microsystem of the invention it is possible for it to be used for example for:
polymer particles, nanoparticles, metal particles; or else animal or vegetable cells, organelles, microorganisms, proteins, DNA molecules, . . . .

In particular, the sorting/concentration device can be applied to sorting Langerhans' islets, fragile cell clusters of size lying in the range 20 µm to 500 µm.

Obtaining a monodispersed population of islets can be advantageous, e.g. when performing pharmacokinetic studies or for encapsulating islets in capsules of matching size.

A device for sorting cell clusters by size is itself an innovative aspect of the invention since given their size and their fragility, it is possible in the prior art to use a single device to enable such clusters to be sorted, but under no circumstances is such a device a microfluidic device.

The microsystem can be sterilized so as to make it possible for it to be used for sorting and concentrating biological particles.

At its inlet, the movement of the fluid may be controlled in pressure or in flow rate.

The device is intended mainly to operate in an aqueous phase or in a culture medium that, from a fluidic point of view, behaves like water.

Nevertheless, it is possible to use it with other types of liquid or with polymer solutions providing the shapes of the liquid recirculation chambers in question are adapted to take account of the density and the viscosity of the liquid in question.

In addition, the sorting device may advantageously be sterilizable.

The invention claimed is:

1. A method of size sorting submillimetric particles or submillimetric particle clusters entrained in a fluid flowing in an axial direction of a main channel, the particles being of density different from the density of the fluid, the method being characterized in that it implements:
in a first region of the main channel, focusing particle by means of at least one focusing device,
said at least one focusing device presenting at least one lateral channel for fluid injection that opens in a wall of the main channel,
such that the focused particles or particle clusters are distributed on flow lines having a position along said wall that depends on their sizes,
and downstream from said region, in a second region of the main channel, collecting said focused particles or particle clusters
in at least one sorting and take-off device in communication with the main channel via an opening that is provided in said wall,
said opening having a dimension that is configured to allow selection of particles or particle clusters as a function of their line of flow,
so that the collected particles or particle clusters are selected by the sorting and take-off device as a function of the size of said particles or particle clusters,
and in that said at least one sorting and take-off device is a recirculation chamber in communication with the main channel and presenting at least one recirculation zone for concentrating the collected particles.

2. A method according to claim 1, characterized in that said recirculation chamber further comprises sequential take-off means.

3. A method according to claim 1, characterized in that said first region is of substantially constant section, and in that said particle focusing is performed by injecting into the main channel a fluid from said focusing device, which presents at least one lateral channel at an angle of incidence α of not less than 5° and preferably of substantially equal to 90° to focus the particles on said wall of said main channel downstream from the region where the lateral injection is performed.

4. A method according to claim 1, characterized in that it implements, opposite from the injection region and facing and/or downstream therefrom, take off by means of at least one take-off channel.

5. A method according to claim 4, characterized in that the size of the take-off channel(s) is less than the size of the finest particles flowing in the main channel.

6. A method according to claim 1, characterized in that the mean speed in the main channel lies in the range 1 mm/s to 50 mm/s, and in that the speed in a recirculation zone lies in the range 5 μn/s to 1000 μm/s.

7. A method according to claim 1, characterized in that said at least one recirculation chamber is coupled to a leakage pumping channel.

8. A method according to claim 7, characterized in that the leakage flow in the leakage pumping channel takes place continuously at an adjustable rate in such a manner as to enable the size of the particles to be selected.

9. A method according to claim 8, characterized in that the flow rate in a leakage pumping channel lies in the range 0.1 μL/h to 500 μL/h.

10. A method according to claim 1, characterized in that it presents a plurality of said sorting and take-off devices in cascade arranged in such a manner as to collect particles of increasing sizes.

11. A method according to claim 10, characterized in that at least one additional focusing device is placed between two of said sorting and take-off devices in cascade.

12. A method according to claim 1, characterized in that it includes at least one row of pillars, the row being inclined relative to the axis of the main channel and extending between said wall of the main channel along which said focusing takes place and the opposite wall to deflect particles of diameter greater than a given diameter Dc, and in that it includes a recirculation chamber opening out into said opposite wall of the main channel in the vicinity of and upstream from the row of pillars.

13. A method according to claim 12, characterized in that a said row of pillars is disposed downstream from said at least one focusing device and between the focusing device and said recirculation chamber.

14. A method according to claim 12, characterized in that the row of pillars is disposed between two of said recirculation chambers.

15. A method according to claim 1, characterized in that it includes an enlarged region of the main channel constituting said recirculation chamber.

16. A method according to claim 15, characterized in that the enlarged region of the main channel includes at least one upstream wall substantially perpendicular to the flow axis of the fluid in the main channel.

17. A method according to claim 1, characterized in that said at least one recirculation chamber is of pseudo-rectangular, circular, or polygonal shape, this recirculation chamber being in communication with the main channel via an opening.

18. A device for sorting particles entrained in a fluid flowing in an axial direction of a main channel, the device being characterized in that
the main channel presents
  a first region presenting at least one focusing device, and
  a second region situated downstream from said first region and presenting at least one take-off device,
said at least one focusing device
  presenting at least one lateral channel for fluid injection that opens in a wall of the main channel,
  for focusing the particles along the wall of the main channel such that the focused particles are distributed on flow lines having a position along said wall that depends on their size,
said at least one take-off device
  forming a recirculation chamber in communication with an opening that is provided in said wall of the main channel and
  presenting at least one recirculation zone for concentrating the collected particles,
  wherein said opening has a dimension that is configured to allow selection of the particles as a function of their flow line.

* * * * *